United States Patent
Nzike et al.

(10) Patent No.: US 10,376,646 B2
(45) Date of Patent: Aug. 13, 2019

(54) CARTRIDGE HOLDER AND METHOD FOR ASSEMBLING A CARTRIDGE UNIT FOR A DRUG DELIVERY DEVICE

(71) Applicant: Sanofi-Aventis Deutschland GmbH

(72) Inventors: Philippe Nzike, Frankfurt am Main (DE); Steffen Raab, Frankfurt am Main (DE); Uwe Dasbach, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/815,977

(22) Filed: Aug. 1, 2015

(65) Prior Publication Data

US 2015/0335824 A1 Nov. 26, 2015

Related U.S. Application Data

(63) Continuation of application No. 13/812,028, filed as application No. PCT/EP2011/063444 on Aug. 4, 2011, now Pat. No. 9,867,945.

(Continued)

(30) Foreign Application Priority Data

Sep. 2, 2010 (EP) ..................... 10174999

(51) Int. Cl.
*A61M 5/31* (2006.01)
*A61M 5/315* (2006.01)
(Continued)

(52) U.S. Cl.
CPC ........ *A61M 5/315* (2013.01); *A61M 5/14566* (2013.01); *A61M 5/24* (2013.01);
(Continued)

(58) Field of Classification Search
CPC ........ A61J 1/062; A61J 1/2096; A61J 1/1418; A61J 1/201; A61M 2005/2411;
(Continued)

(56) References Cited

U.S. PATENT DOCUMENTS 533,575 A 2/1895 Wilkens
2,726,656 A * 12/1955 Lockhart ............... A61J 1/2089
134/58 D (Continued)

FOREIGN PATENT DOCUMENTS

CA 2138528 12/1998
CA 2359375 A1 7/2000
(Continued)

OTHER PUBLICATIONS

Communication of a Notice of Opposition for European Patent Application No. 11741207.2 dated Feb. 24, 2015.
(Continued)

*Primary Examiner* — Scott J Medway
(74) *Attorney, Agent, or Firm* — Fish & Richardson P.C.

(57) ABSTRACT

A cartridge holder (4) for retaining a cartridge (5) comprising a distal end and a proximal end being spaced apart from one another in the direction of an axis, an interior (50) which is suitable to receive and retain a cartridge (5) in a cartridge retaining section (47B) of the interior (50), and a main part (47) and at least one protrusion (39) which is moveably connected to the main part (47). The protrusion (39) is arranged to define the radial extension of a subsection (10) of the interior (50), wherein the subsection (10) is arranged at an axial position which is further away from the distal end than the cartridge retaining section (47B). Furthermore, the protrusion (39) is arranged to vary the radial extension of the subsection (10) when the protrusion (39) is moved with respect to the main part (47). Moreover, a method for securing a cartridge (5) in a cartridge holder (4) is proposed.

32 Claims, 5 Drawing Sheets

Related U.S. Application Data

Figure 1:
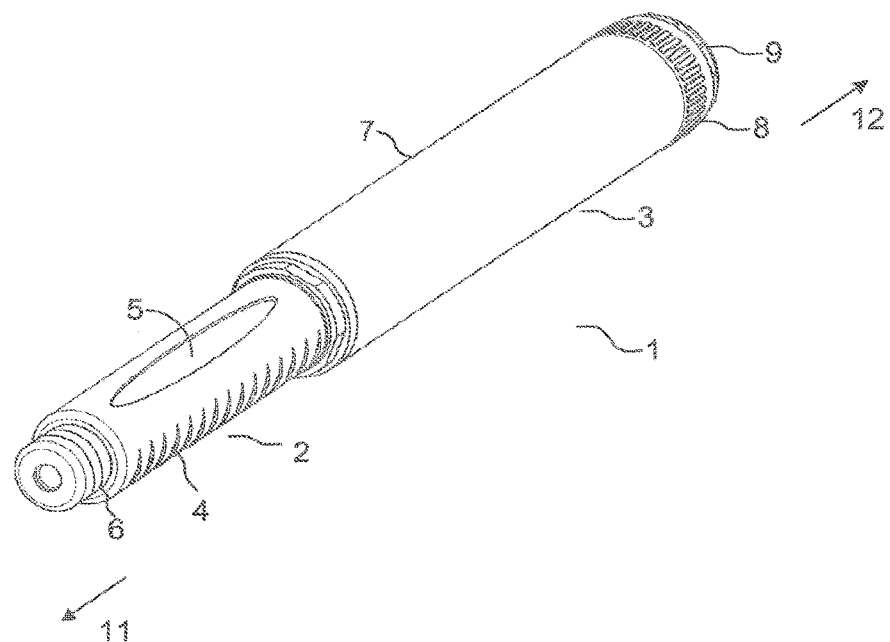

(60) Provisional application No. 61/371,237, filed on Aug. 6, 2010.

(51) Int. Cl.
*A61M 5/145* (2006.01)
*A61M 5/24* (2006.01)
*B65D 25/02* (2006.01)

(52) U.S. Cl.
CPC .... *A61M 5/31515* (2013.01); *A61M 5/31551* (2013.01); *A61M 5/31585* (2013.01); *B65D 25/02* (2013.01); *A61M 5/3146* (2013.01); *A61M 5/31593* (2013.01); *A61M 2005/244* (2013.01); *A61M 2005/2407* (2013.01); *A61M 2005/2437* (2013.01); *A61M 2005/2444* (2013.01); *A61M 2207/00* (2013.01)

(58) Field of Classification Search
CPC ............... A61M 5/24; A61M 5/31553; A61M 2005/2407; A61M 5/31541; A61M 5/31585
See application file for complete search history.

(56) References Cited

U.S. PATENT DOCUMENTS

| | | | |
|---|---|---|---|
| 4,664,653 A * | 5/1987 | Sagstetter | A61M 5/24 604/192 |
| 4,865,591 A | 9/1989 | Sams | |
| 5,092,842 A * | 3/1992 | Bechtold | A61M 5/20 604/135 |
| 5,226,895 A | 7/1993 | Harris | |
| 5,226,896 A | 7/1993 | Harris | |
| 5,244,465 A * | 9/1993 | Michel | A61M 5/24 604/187 |
| 5,279,586 A | 1/1994 | Balkwill | |
| 5,304,152 A | 4/1994 | Sams | |
| 5,320,609 A | 6/1994 | Haber et al. | |
| 5,334,162 A | 8/1994 | Harris | |
| 5,372,590 A * | 12/1994 | Haber | A61M 5/002 604/110 |
| 5,378,233 A | 1/1995 | Haber et al. | |
| 5,383,865 A | 1/1995 | Michael | |
| 5,391,157 A | 2/1995 | Harris et al. | |
| 5,505,704 A | 4/1996 | Pawelka et al. | |
| 5,582,598 A | 12/1996 | Chanoch | |
| 5,584,815 A * | 12/1996 | Pawelka | A61M 5/19 604/135 |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A * | 7/1999 | Bendek | A61M 5/24 604/207 |
| 5,957,896 A | 9/1999 | Bendek et al. | |
| 5,961,495 A | 10/1999 | Walters et al. | |
| 5,984,900 A * | 11/1999 | Mikkelsen | A61M 5/24 604/135 |
| 6,123,688 A * | 9/2000 | Botich | A61M 5/24 604/110 |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,585,698 B1 * | 7/2003 | Packman | A61M 5/24 604/207 |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,186,233 B2 | 5/2012 | Joung et al. | |
| 8,636,704 B2 * | 1/2014 | Shang | A61M 5/2033 604/187 |
| 9,272,096 B2 * | 3/2016 | Schneider | A61M 5/31543 |
| 2002/0120235 A1 | 8/2002 | Enggaard | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2006/0153693 A1 | 7/2006 | Fiechter et al. | |
| 2007/0016143 A1 | 1/2007 | Miller et al. | |
| 2007/0123829 A1 | 5/2007 | Atterbury et al. | |
| 2009/0275916 A1 * | 11/2009 | Harms | A61M 5/24 604/506 |
| 2010/0036320 A1 * | 2/2010 | Cox | A61M 5/31593 604/135 |
| 2010/0042054 A1 * | 2/2010 | Elahi | A61M 5/24 604/211 |
| 2010/0268171 A1 * | 10/2010 | Moller | A61M 5/31551 604/246 |
| 2011/0034902 A1 * | 2/2011 | Markussen | A61M 5/3156 604/506 |
| 2011/0049181 A1 * | 3/2011 | Lutz | A61J 1/2096 222/137 |
| 2011/0087164 A1 * | 4/2011 | Mosler | A61J 1/2089 604/87 |
| 2012/0143146 A1 * | 6/2012 | Strehl | A61M 5/31511 604/208 |
| 2013/0006192 A1 * | 1/2013 | Teucher | A61M 5/24 604/201 |
| 2013/0023831 A1 * | 1/2013 | Helmer | A61M 5/24 604/208 |
| 2013/0204187 A1 * | 8/2013 | Avery | A61M 5/24 604/111 |
| 2013/0204193 A1 * | 8/2013 | Holmqvist | A61M 5/20 604/189 |
| 2013/0231614 A1 * | 9/2013 | Cross | A61M 5/3243 604/198 |
| 2013/0289488 A1 * | 10/2013 | Riess | A61M 5/24 604/189 |
| 2015/0018776 A1 * | 1/2015 | Schenker | A61M 5/2033 604/207 |
| 2015/0119809 A1 * | 4/2015 | Loof | A61M 5/24 604/187 |

FOREIGN PATENT DOCUMENTS

| | | |
|---|---|---|
| EP | 0496141 A1 | 7/1992 |
| EP | 0897729 A2 | 2/1999 |
| EP | 0937471 A2 | 8/1999 |
| EP | 0937476 A2 | 8/1999 |
| EP | 1776975 A2 | 4/2007 |
| EP | 1923083 A1 | 5/2008 |
| WO | 9324160 A1 | 12/1993 |
| WO | 9307922 A1 | 4/1999 |
| WO | 9938554 A1 | 8/1999 |
| WO | 0230495 A2 | 4/2002 |
| WO | 02092153 A2 | 11/2002 |
| WO | 03080160 A1 | 10/2003 |
| WO | 2006084876 A1 | 8/2006 |

OTHER PUBLICATIONS

Professional Article: Andropen—Preset self-injection pen for intracavernous auto-injection therapy in erectile impotence; published in the World Journal of Urology, vol. 8, Issue 2, 1990; Springer Vertlag.

Photos of the Self-Injection Pen "Andropen" (article 117(1)(f) EPC).

(56) References Cited

OTHER PUBLICATIONS

"Pen-injectors for medical use—Part 1: Pen-injectors—Requirements and test methods," International Standard, reference number. ISO 11608-1:2000(E), first edition Dec. 15, 2000, 32 pages.

* cited by examiner

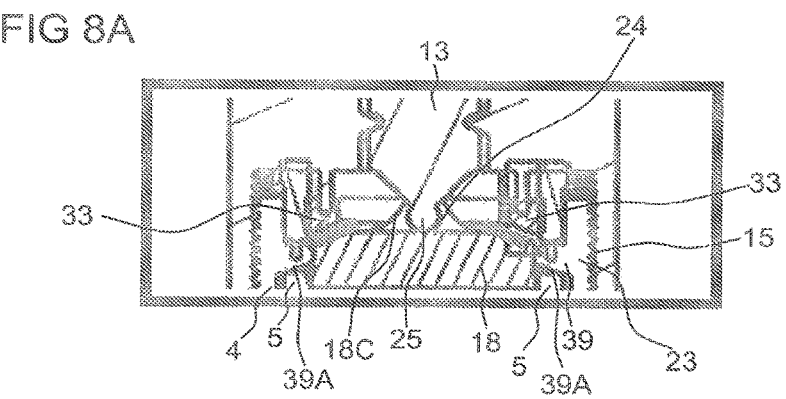
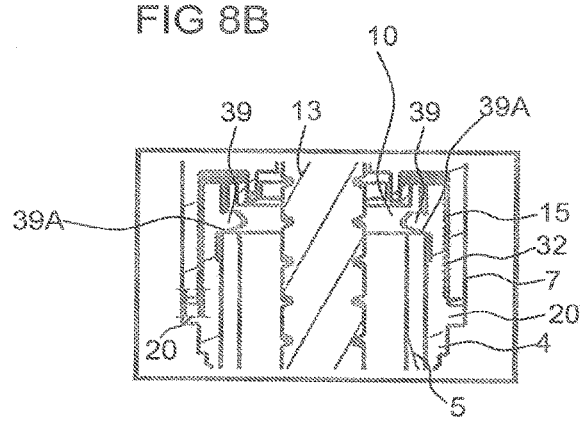
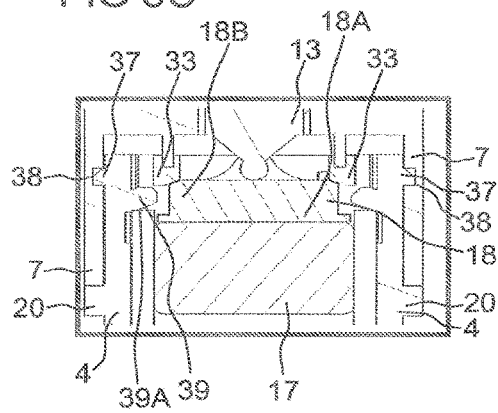
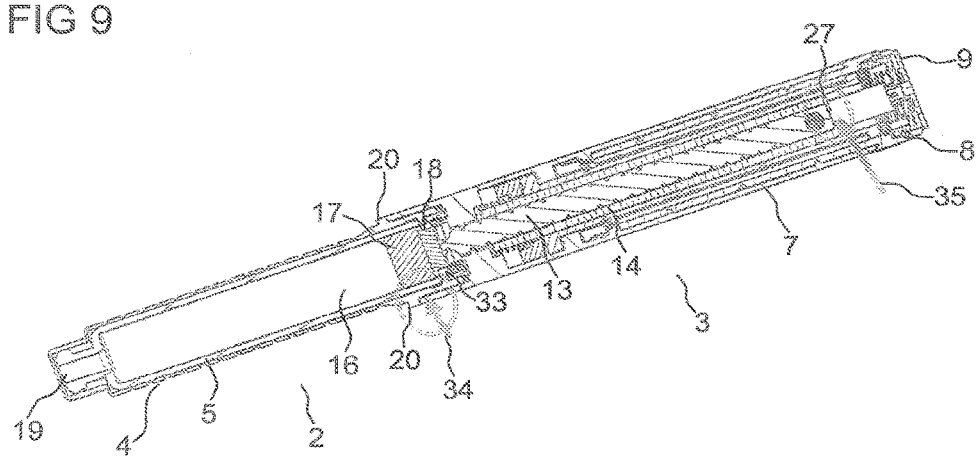

CARTRIDGE HOLDER AND METHOD FOR ASSEMBLING A CARTRIDGE UNIT FOR A DRUG DELIVERY DEVICE

CROSS REFERENCE TO RELATED APPLICATIONS

The present application is a continuation application of U.S. patent application Ser. No. 13/812,028, filed Sep. 5, 2013, which is a 371 of International Patent Application No. PCT/EP2011/063444, filed Aug. 4, 2011 which claims the benefit of U.S. Provisional Patent Application No. 61/371,237, filed Aug. 6, 2010 and European Patent Application No 10174999.2, filed Sep. 2, 2010 the entire contents of which are incorporated entirely herein by reference.

This disclosure relates to a cartridge holder for a drug delivery device. The disclosure further relates to a method for securing a cartridge in a cartridge holder for a drug delivery device.

In a drug delivery device, often, a piston or bung within a cartridge that contains a drug is provided. The piston is displaced with respect to the cartridge by a piston rod for delivering a dose of the drug from the cartridge. In general, it is desirable that the delivered dose of the drug matches the dose which was previously set by a user, i.e. the dose accuracy of the device should be high.

A drug delivery device is described in document EP 1 923 083 A1, for example.

It is an object of the present disclosure to facilitate provision of a novel, preferably an improved, drug delivery device, for example a device with high dose accuracy.

This object may be achieved by the subject matter of the independent claims. Further features and advantageous embodiments are the subject matter of the dependent claims.

According to one aspect a cartridge holder for a drug delivery device is provided. The cartridge holder may be adapted for retaining a cartridge. The cartridge holder may comprise a distal end. The cartridge holder may comprise a proximal end. The distal end and the proximal end are expediently spaced apart from one another in the direction of an axis. The axis may be the main longitudinal axis of the cartridge holder. The cartridge holder comprises an interior. The interior is expediently suitable to receive and retain a cartridge. The interior may comprise a cartridge retaining section. The cartridge retaining section may be adapted to retain the cartridge. The cartridge holder may comprise a main part. The main part may comprise the cartridge retaining section.

The cartridge holder may comprise at least one protrusion. The protrusion is expediently moveably connected to the main part. The protrusion may be adapted to be moved in a radial outward and/or radial inward direction with respect to the axis and, preferably, with respect to the main part. The protrusion may be arranged to define the radial extension of a subsection of the interior. The subsection is preferably arranged at an axial position which is further away from the distal end of the cartridge holder than the cartridge retaining section. Furthermore, the protrusion may be arranged to vary, e.g. to increase and/or to decrease, the radial extension of the subsection when the protrusion is moved with respect to the main part.

The protrusion may be adapted to reduce the radial extension of the subsection such that a cartridge is prevented from being moved into the cartridge retaining section when it is outside of the cartridge holder and/or out of the cartridge retaining section if the cartridge is already arranged in the cartridge retaining section. Accordingly, movement of the protrusion with respect to the main part may be necessary for inserting the cartridge into the cartridge holder and for retrieving the cartridge from the cartridge holder. Unintentional movement of the cartridge with respect to the cartridge holder may be prevented by means of the protrusion. In other words, the inserted cartridge may be held in a stable position with respect to the cartridge holder by means of the protrusion. Dose accuracy may be increased in this way.

A further aspect relates to a cartridge unit. The cartridge unit may be suitable for being secured to a drive unit to form a drug delivery device. The cartridge unit may comprise a cartridge holder, preferably one as described above. The cartridge unit may comprise a cartridge. The cartridge may contain a drug. A bung may be retained within the cartridge. The bung may seal the cartridge proximally. The cartridge may be arranged and retained within the cartridge retaining section of the cartridge holder. The cartridge unit may comprise a drive part. The drive part may be configured to drive the bung distally with respect to the cartridge. The radial extension of the subsection may be less than the radial dimension, e.g. an outer diameter, of the cartridge. The cartridge and the drive part may be retained in the cartridge holder by means of the protrusion. The cartridge may be secured, preferably releasably secured, against proximal displacement with respect to the cartridge holder out of the cartridge retaining section by mechanical cooperation of the cartridge and the protrusion.

A further aspect relates to a method for securing a cartridge in a cartridge holder. Therein, the cartridge is provided. A bung may be retained within the cartridge. The bung may seal the cartridge proximally. In another step, the cartridge holder is provided. The cartridge holder may comprise a distal end and a proximal end. The distal end and the proximal may be spaced apart from one another in the direction of an axis. The cartridge holder may comprise an interior. The cartridge holder may be provided with at least one protrusion. The protrusion may protrude radially inwardly from the cartridge holder. The protrusion expediently defines the radial extension of a subsection of the interior. The subsection may be arranged further away from the distal end of the cartridge holder than the cartridge retaining section. The radial extension may be smaller than a radial dimension of the cartridge such that the cartridge is prevented from being guided from the proximal end of the cartridge holder into the cartridge retaining section. In a further step, the protrusion may be moved, preferably in the radial outward direction, with respect to the cartridge holder such that the radial extension of the subsection is increased. Afterwards, the cartridge may be guided past the protrusion into the cartridge retaining section of the cartridge holder. In a further step the protrusion may be moved, preferably in the radial inward direction, with respect to the cartridge holder to decrease the radial extension of the subsection. The radial extension may be decreased such that the cartridge is secured against proximal displacement with respect to the cartridge holder by mechanical cooperation of the cartridge and the protrusion.

Before the protrusion is moved with respect to the cartridge holder, the cartridge is prevented from being inserted into the cartridge retaining section by means of the protrusion. The protrusion is moved, preferably in the radial outward direction, with respect to the cartridge holder to increase the radial extension of the subsection and, hence, to allow insertion of the cartridge from the proximal end of the cartridge holder through the subsection into the cartridge retaining section. When the protrusion is moved in the opposite direction with respect to the cartridge holder, e.g.

the radial inward direction, the radial extension of the subsection is decreased and, hence, the inserted cartridge may be, preferably releasably, secured against movement, in particular proximal movement, with respect to the cartridge holder. Slipping of the cartridge out of the cartridge holder, which may damage the cartridge, may be prevented in this way. As the cartridge is secured against relative movement with respect to the cartridge holder, provision of a drug delivery device having high dose accuracy is facilitated.

A further aspect relates to a drug delivery device. The drug delivery device may comprise a cartridge unit, preferably one as described above. The drug delivery device may comprise a drive unit. The cartridge unit may be suitable to be secured, preferably releasably secured, to the drive unit. The drive unit may comprise a housing. The housing may have a distal end and a proximal end. A piston rod may be retained in the housing. The piston rod may be arranged to be driven distally with respect to the housing. The piston rod may be configured to displace the drive part distally with respect to the cartridge for dispensing a dose of the drug. The piston rod may be arranged in a proximal stop position with respect to the housing such that proximal displacement of the piston rod beyond the proximal stop position is prevented by means of mechanical cooperation of the piston rod and at least one proximal stop member of the drive unit. The piston rod may be operatively connected to the drive part. The drive part may abut the bung.

In an assembled state of the drug delivery device, play between moveable components of the cartridge unit, e.g. the cartridge holder and the cartridge, as well as play between moveable components of the drive unit may be removed. User-operates steps, e.g. priming steps, for removing play and for making the device ready for operation may be redundant. In this way, a device ready to dispense a full dose may be provided comprising, in particular, a full cartridge which is secured against movement with respect to the cartridge holder. Hence, a user-friendly drug delivery device is achieved providing high dose accuracy.

According to an embodiment, the cartridge holder comprises a moveable part. The moveable part is connected, preferably resiliently connected, to the main part. The protrusion may be, preferably rigidly, connected to the moveable part. The protrusion may be configured such that the radial extension of the subsection decreases in the proximal direction at least partially over the axial extension of the protrusion.

The protrusion preferably extends towards the, preferably proximal, end of the cartridge holder. As seen in plan view onto the proximal end of the cartridge holder from the outside of the cartridge holder, the protrusion may protrude into the interior, in particular into the subsection of the interior of the cartridge holder. Accordingly, a user can realize at once, that the cartridge is prevented from being inserted into the cartridge retaining section and that the protrusion must be moved, preferably in the radial outward direction, with respect to the cartridge holder in order to insert the cartridge. When the cartridge was inserted into the cartridge holder and the protrusion was moved in the opposite, e.g. the radial inward, direction the user can realize at once that the cartridge was properly inserted and, thus, secured against proximal displacement with respect to the cartridge holder. In this way, a user-friendly and easily handled drug delivery device is achieved.

According to an embodiment, the main part comprises two or more axially extending cut-outs. The moveable part may be formed between two cut-outs. An engaging means, e.g. a thread, may be provided in at least a portion of an outer surface of the moveable part. The engaging means may be adapted and arranged to secure the cartridge holder to a drive unit.

Preferably, the engaging means and the moveable part are formed unitarily. No additional components are necessary for integrating the moveable part into the drug delivery device. In this way, provision of a space-saving and cost effective drug delivery device is facilitated.

According to an embodiment, the cartridge holder comprises two or more protrusions. The respective protrusion may be adapted to be moved with respect to the main part to vary, e.g. to increase or decrease, the radial extension of the subsection. The radial extension may be defined by at least two of the protrusions.

According to an embodiment, the protrusion comprises an oblique side face. The oblique side face may be configured to bear against a proximal edge of the cartridge such that the cartridge is expediently held in place with respect to the cartridge holder by means of the oblique side face.

When delivering the set dose, proximal displacement of the cartridge with respect to the cartridge holder may decrease dose accuracy. Due to mechanical cooperation of the cartridge and the oblique side face, the cartridge may be secured against displacement, in particular proximal displacement, with respect to the cartridge holder. Dose accuracy may be increased in this way. User-operated steps, e.g. priming steps, to remove play between the cartridge and the cartridge holder may be redundant.

According to an embodiment, the protrusion comprises an oblique side face. Before the cartridge is secured in the cartridge holder, a measure for a, preferably axial, manufacturing tolerance of at least one of or both of the cartridge holder and the cartridge may be determined. Afterwards, the oblique side face may be formed with a, preferably axial, extension which is derived from the measure.

Accordingly, a length of the oblique side face, in particular the length of the projection of the oblique side face onto the axis, may be adapted to the, preferably maximum axial, manufacturing tolerance of the cartridge and/or the cartridge holder. In this way, the cartridge may be securable in a stable position with respect to the cartridge holder when the protrusion is moved, preferably in the radial inward direction, with respect to the cartridge holder due to mechanical cooperation of the cartridge and the oblique side face. Dose accuracy may be increased in this way.

According to an embodiment, the drive part comprises an interaction section. The interaction section may be arranged between the protrusion and the bung. A radial dimension of the interaction section, e.g. an outer diameter, may be greater than or equal to the radial extension of the subsection such that the drive part is retained in the cartridge holder by means of mechanical cooperation of the interaction section and the protrusion.

The interaction section may comprise or may be embodied as a flange protruding radially outwardly from the drive part. The interaction section may prevent removal of the drive part out of the cartridge holder once the cartridge is secured against proximal displacement with respect to the cartridge holder. Additional steps for securing the drive part in the cartridge holder may be redundant. Hence, a user-friendly drug delivery device is achieved.

According to an embodiment, the drive part comprises a connection section. The connection section may comprise a connection means. The connection means may be adapted and arranged to connect the drive part with a piston rod of a separate drive unit. The connection means may radially overlap with the subsection.

The connection section, in particular the connection means, may be accessible from the outside of the cartridge holder. Accordingly, when securing the cartridge unit to the drive unit, the piston rod and the drive part may be connectable by means of mechanical cooperation of the connection means and a mating connection means of the piston rod. Play between the piston rod and the drive part may thus be avoided.

According to an embodiment, the drive part comprises a transition section. The transition section may be arranged between the interaction section and the connection section. A radial dimension of the transition section, e.g. an outer diameter, may be less than the radial extension of the subsection.

The transition section may extend proximally beyond the protrusion. As the outer diameter of the transition section is preferably smaller than the axial extension of the subsection, the drive part may be easily moveable with respect to the protrusion when the cartridge is secured against proximal displacement with respect to the cartridge holder. In particular, the drive part may be moveable such that the drive part, in particular a distal surface of the drive part, abuts the bung.

According to an embodiment, the drive unit comprises a deformable member. The deformable member may be arranged radially offset from the axis. When the cartridge unit is secured to the drive unit, a proximal surface of the drive part may mechanically cooperate with the deformable member. Thereby, the deformable member may be deformed. A distal surface of the drive part may abut the bung when the cartridge unit is secured to the drive unit.

The deformable member may be a plastically deformable member. Alternatively, the deformable member may be an elastically deformable deflectable member. The deformable member may be deformed by mechanical cooperation of the deformable member and the proximal surface of drive part when the cartridge unit is secured to the drive unit.

According to an embodiment, a method for assembling a drug delivery device is provided. At first, a cartridge unit may be provided. The cartridge unit may have been assembled as described above. Further, a drive unit may be provided. The drive unit may comprise a housing. The housing may have a distal end and a proximal end. A piston rod may be retained in the housing. The drive unit may comprise a deformable member. The deformable member is expediently adapted and arranged to be deformed when the cartridge unit is secured to the drive unit. An axial extension of the deformable member in an undeformed state may be greater than or at least equal to the axial extension of the oblique side face. In a next step, the piston rod may be positioned in a proximal stop position with respect to the housing. Proximal displacement of the piston rod beyond the proximal stop position may be prevented, e.g. by means of at least one proximal stop member of the drive unit mechanically cooperating with the piston rod. Afterwards, the cartridge unit, in particular with the cartridge secured against proximal displacement, may be secured, preferably releasably secured, to the drive unit. The cartridge unit may be secured, preferably releasably secured, to the drive unit under deformation of the deformable member.

The axial extension of the undeformed deformable member may be such that accumulated axial manufacturing tolerances of the cartridge unit and of the drive unit may be compensatable by means of the deformable member when the cartridge unit is secured to the drive unit. Accordingly, due to deformation of the deformable member, the cartridge unit is secured to the drive unit such that there is no gap between the cartridge unit and the drive unit. User-operated steps, e.g. priming steps, to remove a gap may be redundant. Thus, provision of a drug delivery device having high dose accuracy is facilitated.

According to an embodiment, the cartridge unit comprises a drive part. The piston rod may be adapted to be connectable to the drive part. Additionally, the piston rod may be adapted to drive the drive part in the distal direction with respect to the cartridge. When the cartridge unit is secured to the drive unit, the piston rod may be operatively connected to the drive part. Additionally, when the cartridge unit is secured to the drive unit, the drive part may abut the bung.

Accordingly, there may be no play between the bung and the drive part and, hence, the piston rod, when the cartridge unit was secured to the drive unit. Dose accuracy may be increased in this way. User-operated steps for removing play may be redundant.

According to a preferred embodiment, a cartridge holder for retaining a cartridge is provided, the cartridge holder comprising
- a distal end and a proximal end being spaced apart from one another in the direction of an axis,
- an interior which is suitable to receive and retain a cartridge in a cartridge retaining section of the interior, and
- a main part and at least one protrusion which is moveably connected to the main part.

The protrusion is arranged to define the radial extension of a subsection of the interior, wherein the subsection is arranged at an axial position which is further away from the distal end than the cartridge retaining section, and wherein the protrusion is arranged to vary the radial extension of the subsection when the protrusion is moved with respect to the main part.

According to a further preferred embodiment, a method for securing a cartridge in a cartridge holder is provided, the method comprising the following steps:
- providing the cartridge, a bung being retained within the cartridge, the bung sealing the cartridge proximally,
- providing the cartridge holder, the cartridge holder comprising an interior, a distal end and a proximal end being spaced apart from one another in the direction of an axis and the cartridge holder being provided with at least one protrusion protruding radially inwardly from the cartridge holder, the protrusion defining the radial extension of a subsection of the interior, which subsection is arranged further away from the distal end of the cartridge holder than the cartridge retaining section, the radial extension being smaller than a radial dimension of the cartridge such that the cartridge is prevented from being guided from the proximal end of the cartridge holder into the cartridge retaining section,
- moving the protrusion with respect to the cartridge holder such that the radial extension of the subsection is increased,
- guiding the cartridge past the protrusion into the cartridge retaining section of the cartridge holder,
- moving the protrusion with respect to the cartridge holder to decrease the radial extension of the subsection such that the cartridge is secured against proximal displacement with respect to the cartridge holder by mechanical cooperation of the cartridge and the protrusion.

Due to the cartridge holder and the method described above provision of an easily handled drug delivery device is facilitated. User-operated steps for priming the device, e.g. steps for making the device ready for operation and, in particular for removing play between moveable components, e.g. the cartridge holder and the cartridge, may be redundant. The cartridge may be held in a well-defined and stable position with respect to the cartridge holder by means of mechanical cooperation of the cartridge and the protrusion. Relative movement of the cartridge and the cartridge holder may be prevented. Accordingly, the device may exhibit high dose accuracy.

Of course, features described above in connection with different aspects and embodiments may be combined with each other and with features described below.

Further features and refinements become apparent from the following description of the exemplary embodiments in connection with the accompanying figures.

Figure 2:
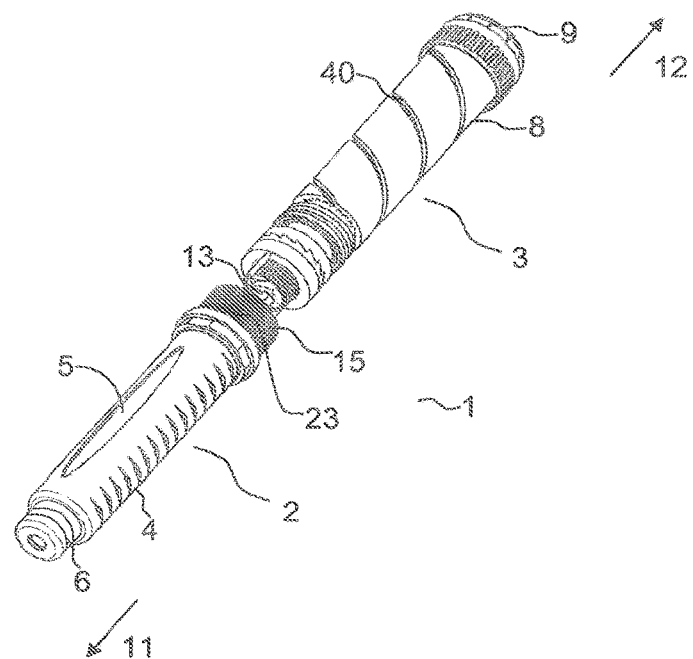
Figure 3:
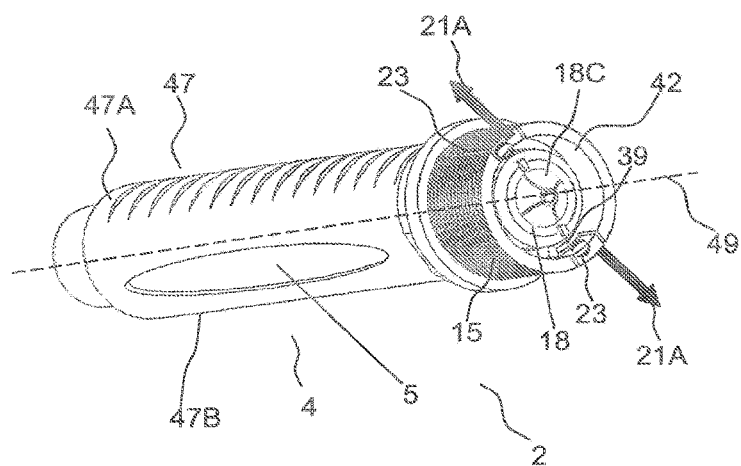
Figure 4A:
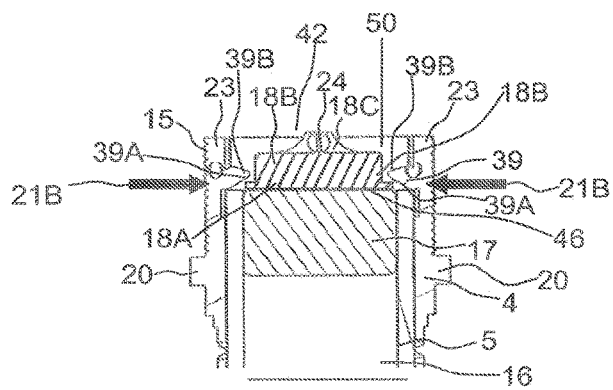
Figure 4B:
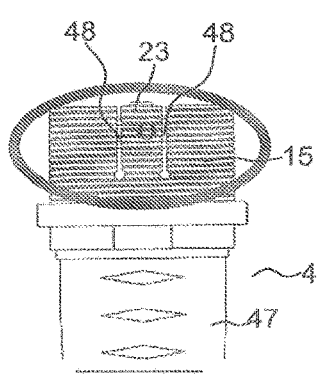
Figure 5:
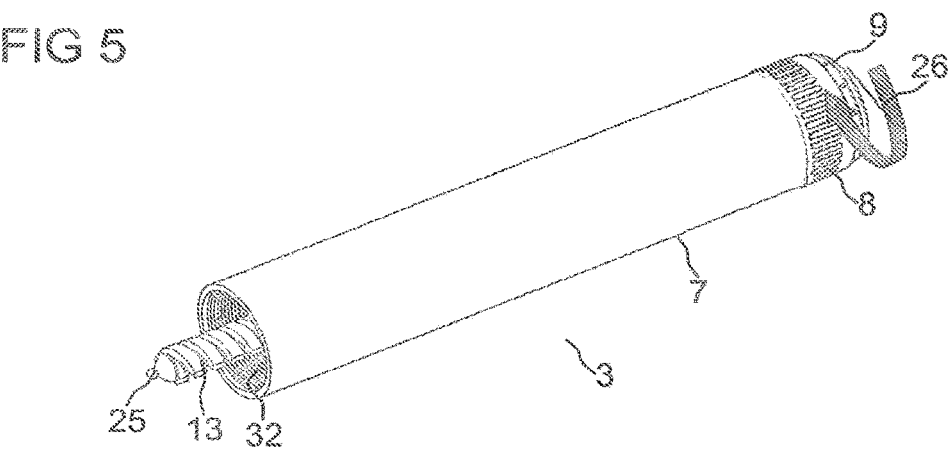
Figure 6A:
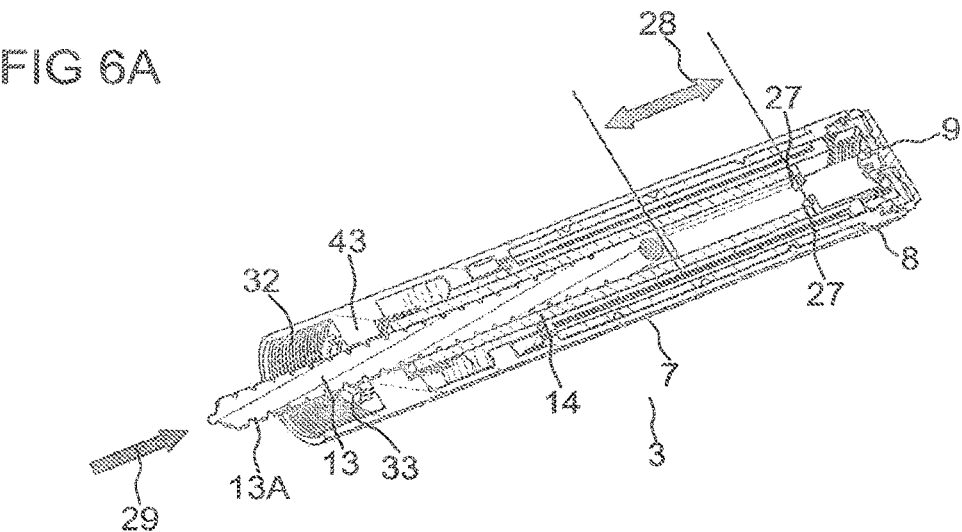
Figure 6B:
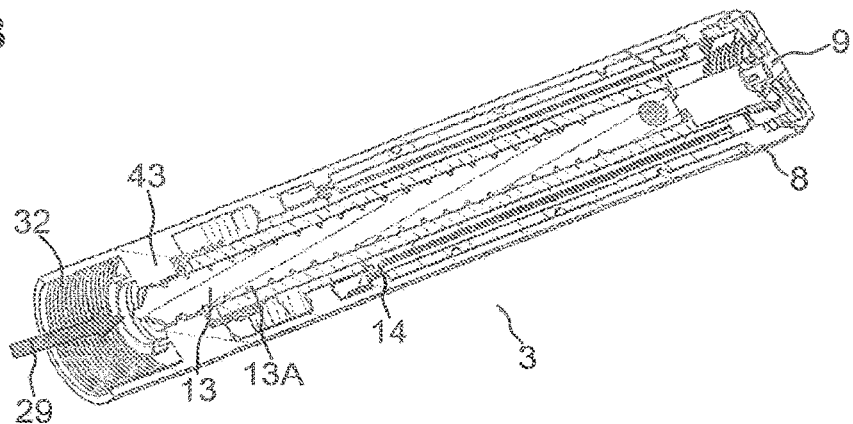
Figure 7A:
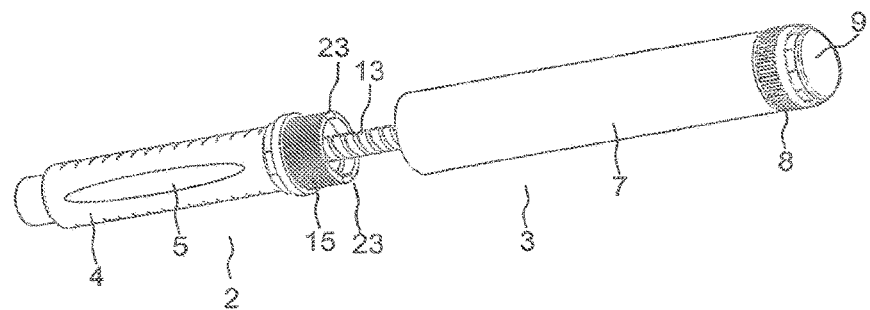
Figure 7B:
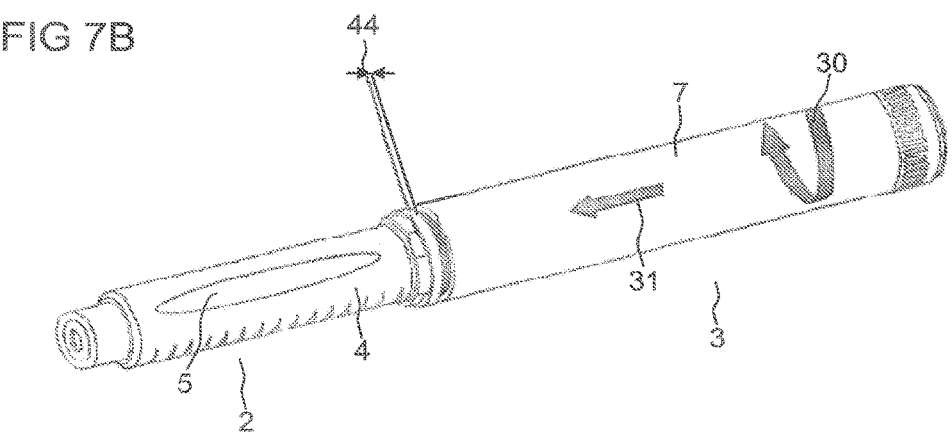
Figure 7C:
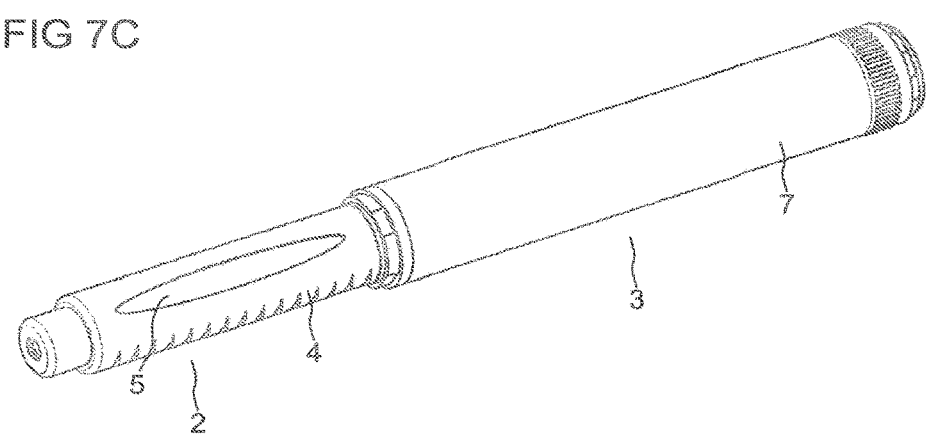

FIG. 1 schematically shows a perspective side view of an exemplary embodiment of a drug delivery device, FIG. 2 schematically shows a part the drug delivery device of FIG. 1, FIG. 3 schematically shows a perspective side view of an embodiment of a cartridge unit for a drug delivery device, FIG. 4A schematically shows a sectional view of a part of the cartridge unit of FIG. 3, FIG. 4B schematically shows an outer view of a part of the cartridge unit of FIG. 3, FIG. 5 schematically shows a perspective side view of an embodiment of a drive unit for a drug delivery device, FIG. 6A and FIG. 6B schematically show an inner view of the drive unit of FIG. 5 in two different assembly states, FIGS. 7A through 7C schematically show the drug delivery device of FIG. 1 while being assembled and after assembling was completed, FIGS. 8A through 8C schematically show a part of the readily assembled drug delivery device, FIG. 9 schematically shows a sectional view of the drug delivery device of FIG. 7C.

Like elements, elements of the same kind and identically acting elements may be provided with the same reference numerals in the figures.

In FIG. 1, an exemplary embodiment of a drug delivery device 1 is shown. The drug delivery device 1 comprises a cartridge unit 2. The drug delivery device 1 comprises a drive unit 3. The cartridge unit 2 is, releasably or irreleasably, connected to the drive unit 3, for example by means of a threaded engagement or a snap fit connection, which is described in connection with FIGS. 2, 8B and 8C in more detail. The position of the cartridge unit 2 with respect to the drive unit 3 is, for example, determined by means of a stop member (see stop member 20 in FIG. 4A).

The cartridge unit 2 comprises a cartridge holder 4. The cartridge unit 2 comprises a cartridge 5. The cartridge 5 is retained in the cartridge holder 4. The cartridge holder 4 stabilizes the cartridge 5 mechanically. The cartridge 5 may hold one or a plurality of doses of a drug (see drug 16, FIG. 4A). The drug 16 is preferably a liquid medication, comprising, for example, insulin, like short-acting or long-acting insulin, heparin and/or growth hormones.

The cartridge 5 has an outlet (see outlet 19, FIG. 9). The drug 16 can be dispensed from the cartridge 5 through the outlet 19. The outlet 19 may be covered by a septum. The septum may protect the drug 16 against external influences during storage of the cartridge 5. The septum may seal the outlet 19 fluid-tightly.

The cartridge unit 2 comprises a bung (see bung 17, FIG. 4A). The bung 17 is retained within the cartridge 5. The bung 17 is moveable with respect to the cartridge 5. The bung 17 seals the cartridge 5 proximally. Movement of the bung 17 with respect to the cartridge 5 causes the drug 16 to be dispensed from the cartridge 5 through the outlet 19, provided that the septum was opened, e.g. pierced by a needle which may be connectable to the cartridge holder 4 by means of an engaging means 6, e.g. a thread.

Otherwise, e.g. on account of the comparatively incompressible liquid in the cartridge 5, the bung 17 may not be moved significantly towards the outlet 19 which is covered by the septum.

The drive unit 3 comprises a housing 7. The housing 7 is configured to house, fix, protect or guide inner components, e.g. components of a drive mechanism, of the drug delivery device 1. The drug delivery device 1 and the housing 7 have a distal end and a proximal end. The term "distal end" designates that end of the drug delivery device 1 or a component thereof which is or is to be arranged closest to a dispensing end of the drug delivery device 1. The distal end of the device 1 is indicated by arrow 11. The term "proximal end" designates that end of the device 1 or a component thereof which is or is to be arranged furthest away from the dispensing end of the device 1. The proximal end of the device 1 is indicated by arrow 12.

The drive unit 3 comprises a piston rod 13 (not explicitly shown in FIG. 1, see, for example, FIG. 2). The piston rod 13 is designed to transfer axial movement through the drug delivery device 1, for example for the purpose of dispensing the drug 16. In particular, the piston rod 13 is designed to transfer force to the bung 17, thereby pushing the bung 17 in the distal direction with respect to the cartridge 5. The size of the dispensed dose is determined by the distance by which the bung 17 is displaced in the distal direction with respect to the cartridge 5.

The cartridge unit 2 comprises a drive part 18 (not explicitly shown in FIG. 1, see FIG. 4A). The drive part 18 is configured to facilitate interaction between the bung 17 and the piston rod 13 for delivering the set dose which is described in FIG. 4A in more detail. The drive part 18 is connectable to the piston rod 13 (see description of FIGS. 5, 6A and 6B). The piston rod 13 is rotatable with respect to the drive part 18 when the drive part 18 and the piston rod 13 are connected. The drive part 18 is secured against axial movement with respect to the piston rod 13 when the drive part 18 and the piston rod 13 are connected. The drive part 18 may be a bearing member, for example.

The drive unit 3 comprises a drive mechanism. The piston rod 13 is driven distally by the drive mechanism for dispensing a set dose of the drug 16. Any distal movement of the piston rod 13 may cause the drug 16 to be dispensed from the cartridge 5, provided that play between the piston rod 13 and the bung 17 was eliminated before and, in particular, that the septum was opened or removed. The drive mechanism comprises a drive member 14 (not explicitly shown in FIG. 1, see FIGS. 6A and 6B). The piston rod 13 is arranged at least partly within drive member 14. The drive member 14 is rotatable with respect to the housing 7 for delivering the set dose. The drive member 14 is axially displaceable with respect to the housing 7 when setting and when delivering the dose. The drive member 14 may comprise or may be embodied as a drive sleeve. The piston rod 13 comprises an outer thread 13A. Preferably, the outer thread 13A is flattened in an axially extending portion. The drive member 14 comprises a flattened portion arranged along an inner surface of the drive member 14. Preferably, the piston rod 13 is splined to the drive member 14 by mechanical cooperation of the flattened inner portion and the flattened outer thread 13A.

The drive mechanism comprises a dose member 8. The dose member is expediently moveable for setting a dose of drug which is to be delivered by the device. The dose member 8 is rotatable and axially displaceable, e.g. by mechanical cooperation of an outer thread 40 of the dose member 8 and a mating inner thread of the housing 7, with respect to the housing 7 when setting and delivering a dose.

The drive mechanism comprises a dose button 9. Dose button 9 may be part of the dose member 8 or may be a separate member. The dose member 8 is rotatable with respect to the dose button 9. The dose button 9 is configured to be pushed by a user for dispensing the set dose.

The drive member 14 and the dose member 8 are rotationally locked for delivering the set dose, for example via a clutch connection. When setting the dose, the clutch connection may be de-activated, e.g. by means of a spring member (not explicitly shown) keeping mating teeth, e.g. dog teeth, provided on the dose member 8 and the drive member 14 for the clutch connection out of engagement. The clutch connection may be activated by overcoming the force of the spring member, e.g. when pushing the dose button 9 for delivering the set dose.

The drug delivery device 1 may be an injection device. The drug delivery device 1 may be a pen-type device, in particular a pen-type injector. The device 1 may be a disposable or a re-usable device. The device 1 may be configured to dispense fixed doses of the drug 16, in particular doses which may not be varied by the user, or variable, preferably user-settable, doses of the drug 16. The drug delivery device 1 may be a manually, in particular a non-electrically, driven device.

FIG. 2 schematically shows a part the drug delivery device of FIG. 1. In particular, FIG. 2 shows the device 1 without the housing 7.

The cartridge unit 2 comprises an engaging means 15. In the embodiment shown in FIG. 2, engaging means 15 is a thread. The engaging means 15 is provided in a proximal end section of the cartridge holder 4. The drive unit 3 comprises an engaging means 32 (see FIG. 5). Engaging means 32 is arranged in a distal end section of the housing 7. Engaging means 32 is an inner thread, for example. Mechanical cooperation of engaging means 15 and engaging means 32 enables the threaded engagement of the drive unit 3 and the cartridge unit 2 for, preferably releasably, securing the cartridge unit 2 to the drive unit 3. This may facilitate provision of a re-usable drug delivery device 1 as described in connection with FIG. 8B.

FIG. 3 schematically shows a perspective side view of an embodiment of a cartridge unit for a drug delivery device.

FIG. 4A schematically shows a sectional view of a part of the cartridge unit of FIG. 3.

FIG. 4B schematically shows an outer view of a part of the cartridge unit of FIG. 3.

The cartridge unit 2 comprises the previously mentioned cartridge 5. The cartridge unit 2 comprises the previously mentioned cartridge holder 4. The cartridge holder 4 comprises an interior 50 (see FIG. 4A). The cartridge holder 4 comprises an opening 42. The opening 42 is arranged at the proximal end of the cartridge holder 4. The cartridge 5 is guided through the opening 42 into the interior 50 of the cartridge holder 4, in particular into a cartridge retaining section 47B (see FIG. 3) of the cartridge holder 4. The cartridge retaining section 47B may be a part of the interior 50 in which the cartridge 5 is arranged.

The cartridge holder 4 comprises a main part 47 (see FIGS. 3 and 4B). The main part 47 comprises a tubular shape. The main part 47 comprises a radially inwardly directed shoulder portion 47A. The shoulder portion 47A may form a distal end stop face for the cartridge 5 when the cartridge 5 is inserted into the cartridge retaining section 47B. In the distal direction the shoulder portion 47A is followed by the previously mentioned engaging means 6 (see FIG. 1) for connecting a needle to the distal end of the main part 47 of the cartridge holder 4.

The cartridge holder 4 comprises at least one moveable part 23. According to this embodiment, the cartridge holder 4 comprises two moveable parts 23. The two moveable parts 23 are arranged oppositely with respect to one another. Alternatively, the cartridge holder 4 may comprise only one or three or more moveable parts 23.

The respective moveable part 23 is moveably connected to the main part 47. Preferably, the main part 47 and the respective moveable part 23 are formed unitarily. The respective moveable part 23 may be moveable in a radial direction, inwardly and/or outwardly, with respect to a main longitudinal axis 49 (see FIG. 3) of the cartridge holder 4 and with respect to the main part 47. The respective moveable part 23 may be a resilient member or a member which is resiliently mounted to the main part 47, for example. Accordingly, the moveable part 23 may be adapted to be moved back automatically, e.g. by an elastic restoring force, in a opposite direction, e.g. the radial inward direction, than it was moved previously with respect to the main part 47, e.g. in the radial outward direction.

According to the embodiment shown in FIGS. 3, 4A and 4B, the respective moveable part 23 is arranged in the proximal end section of the cartridge holder 4. A portion of the engaging means 15 may be arranged at or may be part of an outer surface of the moveable part 23. The engaging means 15 is provided with at least one cut-out 48. Preferably, the engaging means 15 comprises two pairs of cut-outs 48 as indicated in FIG. 4B. The two pairs are arranged oppositely with respect to each other. The respective cut-out 48 runs along the main longitudinal axis 49 of the cartridge holder 4. The respective cut-out 48 interrupts the engaging means 15. The respective moveable part 23 is formed between two cut-outs 48.

The cartridge holder 4 comprises at least one protrusion 39 (see FIG. 4A). The respective protrusion 39 is moveably connected to the main part 47. The respective protrusion 39 is preferably part of the respective moveable part 23 as shown in FIG. 4A or is connected thereto. The protrusion 39 is rigid, e.g. rigidly connected to the moveable part 23 or rigidly formed. Preferably, the respective moveable part 23 and the protrusion 39 are formed unitarily. The protrusion 39 is arranged between the opening 42 and the cartridge retaining section 47B. The protrusion 39 protrudes radially inwardly from the respective moveable part 23. As seen in plan view onto the opening 42 from the outside of the cartridge holder 4 (see FIG. 3) in the distal direction, the protrusion 39 protrudes into the opening 42.

The protrusion 39 is adapted to define the radial extension of a subsection 10 (see FIG. 8B) of the interior 50 of the cartridge holder 4 with respect to the main longitudinal axis 49. The subsection 10 is arranged at an axial position which is further away from the distal end of the cartridge holder 4 than the cartridge retaining section 47B. The axial position of the subsection 10 is defined by the axial position of the respective protrusion 39. In an initial state of the cartridge unit 2, the radial extension of the subsection 10 may be less than the radial dimension, e.g. an outer diameter, of the cartridge 5 such that the cartridge 5 is prevented from being guided from the proximal end of the cartridge unit 2 through the opening 42 past the protrusion 39 into the cartridge retaining section 47B.

The respective moveable part 23 and, hence, the protrusion 39 is adapted to vary the radial extension of the subsection 10. In particular, the respective moveable part 23 is moved in the radial outward direction with respect to the main longitudinal axis 49 (see arrows 21A, FIG. 3) of the cartridge holder 4 to increase the radial extension of the subsection 10 such that the cartridge 5 can be guided into the cartridge retaining section 47B through the opening 42. Then, the cartridge 5 may be guided into the cartridge retaining section 47B. The respective moveable part 23 and, hence, the protrusion 39 is moved in the radial inward direction with respect to the main longitudinal axis 49 (see arrows 21B in FIG. 4A) to decrease the radial extension of the subsection 10 such that the previously inserted cartridge 5 is, preferably releasably, secured against displacement, in particular proximal displacement, with respect to the cartridge holder 4.

The protrusion 39 comprises a free end 39B. The free end 39B is directed radially inwardly. The protrusion 39 is oriented in the proximal direction as seen in the direction of the radially inwardly directed free end 39B. In particular, the protrusion 39 extends towards the proximal end of the cartridge holder 4 such that the radial extension of the subsection 10 decreases in the proximal direction at least partially over the axial extension of the protrusion 39.

In ordinary drug delivery devices, there may be play between the cartridge 5 and the cartridge holder 4 when the cartridge 5 was inserted into the cartridge holder 4 due to, in particular axial, manufacturing tolerances, e.g. variations if the length, of the cartridge 5 and the cartridge holder 4. Such play may decrease dose accuracy. Hence, play between the cartridge 5 and the cartridge holder 4 must often be removed, e.g. by user-operates steps, for example priming steps, in order to guarantee for high dose accuracy in regular drug delivery devices.

In order to avoid play between the cartridge 5 and the cartridge holder 4 and to avoid user-operated priming steps, the protrusion 39 comprises an oblique side face 39A. The oblique side face 39A is configured to mechanically cooperate with, in particular to bear against, the proximal end, in particular a proximal edge, of the cartridge 5 (see FIG. 4A). In particular, the oblique side face 39A is adapted to bias the cartridge 5 in the distal direction with respect to the cartridge holder 4 and towards the distal end stop face, which is defined by the radially inwardly directed shoulder portion 47A, when the moveable part 23 is moved radially inwardly, e.g. by an elastic restoring force of the resilient moveable part 23 or the resiliently mounted moveable part 23, to secure, preferably releasably secure, the cartridge 5 against proximal and distal displacement with respect to the cartridge holder 4.

A length of the projection of the oblique side face 39A onto the main longitudinal axis 49 may be such that the cartridge 5 is kept in a well-defined and stable position with respect to the cartridge holder 4 by means of mechanical cooperation of the cartridge 5 and the oblique side face 39A when the respective moveable part 23 and, hence, the protrusion 39 was moved radially inwardly. Accordingly, in an assembled state of the cartridge unit 2, the cartridge 5 may be clamped between the distal end stop face and the protrusion 39 such that the cartridge 5 is secured against distal and proximal displacement with respect to the cartridge holder 4. This may help to increase dose accuracy. User-operated steps, e.g. priming steps, which are necessary to remove play between the cartridge 4 and the cartridge holder 5 may be redundant.

The drive part 18 comprises an interaction section 18A. The interaction section 18A is configured to mechanically interact with, in particular to abut, the bung 17. The interaction section 18A is arranged in the distal end section of the drive part 18. The interaction section 18A is arranged between the protrusion 39 and the bung 17. The interaction section 18A comprises a dimension suitable to drive the bung 17 within the cartridge 5. The interaction section 18A comprises a protruding portion. The protruding portion may be a radially outwardly directed flange, for example. A radial dimension, e.g. an outer diameter, of the interaction section 18A is greater than the radial extension of the subsection 10 when the cartridge unit 2 is in the assembled state. In this way, the drive part 18 is, preferably loosely, retained in the cartridge unit 2 by mechanical cooperation of the interaction section 18A and the respective protrusion 39 when the cartridge unit 2 is in the assembled state. In other words, the interaction section 18A and, hence, the whole drive part 18 is prevented from passing the respective protrusion 39 for being removed from the cartridge unit 2 once the cartridge unit 2 is assembled.

The drive part 18 comprises a connection section 18C. The connection section 18C is arranged in the proximal end section of the drive part 18. The connection section 18C comprises a connection means 24. Connection means 24 is a recess, for example, as shown in FIG. 4A. Connection means 24 enables the connection, for example a snap-fit connection, of a distal counterpart (see connection means 25, shown in FIG. 5) of the piston rod 13 and the drive part 18 when the cartridge unit 2 is secured to the drive unit 3, e.g. when assembling the device 1. When the drive part 18 and the piston rod 13 are connected, axial displacement of the drive part 18 with respect to the piston rod 13 may be prevented. However, the piston rod 13 may be rotatable with respect to the drive part 18.

The drive part 18 comprises a transition section 18B. The transition section 18B is arranged between the interaction section 18A and the connection section 18C. Preferably, the interaction section 18A, the transition section 18B and the connection section 18C are formed unitarily. The transition section extends in the proximal direction beyond the respective protrusion 39. The transition section 18B comprises a radial extension, e.g. an outer diameter, which is smaller than the radial extension of the subsection 10 when the cartridge unit 2 is in the assembled state. In this way, the drive part 18 is easily axially displaceable with respect to the cartridge holder 4 when the cartridge unit 2 is in the assembled state.

In the following, operation of assembling the cartridge unit 2, in particular of securing the cartridge 5 in the cartridge holder 4, is described. The said cartridge unit 2 may be suitable for being secured to the drive unit 3 to form a drug delivery device 1, which is explained later on in more detail. Of course, assembly of the cartridge unit 2 as described in the following is performed before assembly of the drug delivery device 1 and, in particular, before connection of the readily assembled cartridge unit 2 and the drive unit 3 takes place.

In a first step, a measure for an axial manufacturing tolerance, e.g. the variation of the length, may be determined for a plurality of identically manufactured previously described cartridges 5. In particular, the measure may comprise the maximum axial manufacturing tolerance for the cartridge 5. Additionally or alternatively, a measure for an axial manufacturing tolerance, e.g. the variation of the length, may be determined for a plurality of identical previously described cartridge holders 4. The measure may comprise the maximum axial manufacturing tolerance for the cartridge holder 4. Furthermore, a length of the oblique side face 39A may be formed such that it is adapted to compensate the maximum manufacturing tolerance, preferably the maximum accumulated manufacturing tolerance, of the cartridge 5 and/or the cartridge holder 4 when the cartridge 5 is secured in the cartridge holder 4. Accordingly, an optimal length of the oblique side face 39A may be greater than or at least equal to the twofold sum of the maximum axial manufacturing tolerances, e.g. the maximum variation of the lengths, of the cartridge 5 and the cartridge holder 4.

In a second step, the previously described cartridge holder 4 is provided.

In a third step, the previously described cartridge 5 is provided.

In a further step, the cartridge 5 is inserted into the cartridge holder 4. Additionally, the drive part 18 is inserted into the cartridge holder 4. For inserting the cartridge 5 into the cartridge holder 4 the respective moveable part 23 is moved radially outwardly with respect to the main longitudinal axis 49 (see arrow 21A in FIG. 3). Thereby, the radial extension of the subsection 10 is increased. The respective moveable part 23 is moved radially outwardly until the radial extension of the subsection 10 is large enough for guiding the cartridge 5 through the opening 42 past the protrusion 39 into the cartridge retaining section 47B. Afterwards or together with the cartridge 5, the interaction section 18A of the drive part 18 may be guided past the protrusion 39.

In a next step, the respective moveable part 23 is moved radially inwardly with respect to the main longitudinal axis 49 as indicated by arrows 21B in FIG. 4A. If the respective moveable part 23 is a resilient or resiliently mounted member, an elastic restoring force may move the moveable part 23 in the radial inward direction. When the respective moveable part 23 is moved radially inwardly, the protrusion 39, in particular the oblique side face 39A, comes into mechanical interaction, in particular abutment, with the proximal edge of the cartridge 5. The radially inwardly directed force that moves the protrusion 39 radially inwardly may be converted into a distally directed force acting on the cartridge 5 by means of the oblique side face 39A interacting with the cartridge 5. Accordingly, the cartridge 5 is secured against displacement with respect to the cartridge holder 4 due to mechanical cooperation of the oblique side face 39A and the cartridge 5. In particular, the cartridge 5 is held in a stable position relative to the cartridge holder 4. Play between the cartridge 5 and the cartridge holder 4 arising from manufacturing tolerances may be removed by means of the oblique side face 39A. Hence, dose accuracy may be increased. User operated steps, e.g. priming steps, for removing play between the cartridge 5 and the cartridge holder 4 may be redundant. The assembled cartridge unit 2 is now ready for being secured to a drive unit 3.

FIG. 5 schematically shows a perspective side view of an embodiment of a drive unit for a drug delivery device.

FIG. 6A and FIG. 6B schematically show an inner view of the drive unit of FIG. 5 in two different assembly states.

In an initial state of the drive unit 3, there may be a gap between the piston rod 13 and the proximal end section of the drive unit 3, in particular the proximal end of the drive member 14. This may result from the piston rod 13 having been displaced distally for emptying a previously present cartridge 5 which was detached or from manufacturing tolerances. The size of the gap may vary. The gap is indicated by arrow 28 in FIG. 6A. The gap is removed before the cartridge unit 2 is secured to the drive unit 3 in order to facilitate high dose accuracy of the drug delivery device 1 which is to be formed.

For this purpose, the piston rod 13 is displaced in the proximal direction with respect to the housing 7. In particular, the piston rod 13 is displaced towards and positioned in a proximal stop position for removing the gap. In the proximal stop position the piston rod 13 abuts at least one proximal stop member (see stop member 27 in FIG. 6A). Proximal stop member 27 is arranged in the proximal end section of the drive member 14, for example. The proximal stop member 27 protrudes radially inwardly from the drive member 14. Proximal stop member 27 may be an inwardly directed flange, for example.

For displacing the piston rod 13 in the proximal stop position, the drive member 14 is rotated with respect to the housing 7, as indicated by arrow 26 in FIG. 5. Upon rotation of the drive member 14 the piston rod 13 is rotated and displaced in the proximal direction with respect to the housing 7 and towards the proximal stop position (see arrow 29 in FIGS. 6A and 6B) due to mechanical interaction of thread 13A of the piston rod 13 and a mating thread arranged at an inner surface of the housing 7. In the proximal stop position further proximal displacement of the piston rod 13 beyond the proximal stop position is prevented due to mechanical cooperation, in particular abutment, of a proximal face of the piston rod 13 and the stop member 27. In the proximal stop position any play between the piston rod 13 and the drive member is removed. Dose accuracy may be increased in this way.

The drive unit 3 comprises a deformable member 33 (see FIG. 6A). The deformable member 33 is configured to mechanically interact with, in particular to abut, the drive part 18 when the cartridge unit 2 is secured to the drive unit 3. The deformable member 33 may be a plastically deformable member. Alternatively, the deformable member 33 may be an elastically deformable deflectable member.

The deformable member 33 is positioned in the distal end section of the drive unit 3. The deformable member 33 is arranged within the housing 7. In particular, the deformable member 33 is arranged radially offset from and preferably circumferentially around a main longitudinal axis of the drive unit 3. The deformable member 33 is secured against displacement with respect to the housing 7. Preferably, the deformable member 33 is glued to the housing 7. The drive unit 3 may comprise two oppositely disposed deformable members 33. Alternatively, the deformable member 33 may be, for example, a, preferably resilient, ring, as indicated in FIGS. 6A and 6B. The ring is arranged around an opening through which the piston rod 13 is guided. The opening may comprise a piece for threadedly coupling the piston rod 13 to the housing 7 (not explicitly shown). Due to the threaded coupling of the piston rod 13 and the housing 7, the piston rod 13 is displaceable in the distal direction for dispensing the set dose. The opening may be formed by an inwardly protruding portion in the housing 7.

When the piston rod 13 is in the proximal stop position the axial position of the deformable member 33 is preferably such that the deformable member 33 is arranged around the distal end of the piston rod 13. In particular, the distal end of the piston rod 13 may be arranged between the distal end of the deformable member 33 and the proximal end of the deformable member 33 or between the distal end of the deformable member 33 and the distal end of a protruding portion 43 arranged within the housing 7 (see FIG. 6B). When the piston rod 13 is in the proximal stop position, the deformable member 33 preferably extends farther in the distal direction with respect to the housing 7 than the piston rod 13. This may help to facilitate mechanical interaction of the deformable member 33 and the drive part 18 when the drive unit 3 is secured to the cartridge unit 2 to compensate a residual distance between the cartridge unit 2 and the drive unit 3 which distance may arise from manufacturing tolerances in the cartridge unit 2 and/or the drive unit 3 and by which distance the drive unit 2 and the cartridge unit 3 may be offset with respect to each other from a desired relative end position.

In an undeformed state, the deformable member 33 may comprise an axial extension which is greater than or at least equal to the length of the oblique surface 39A. In particular, the axial extension may be greater than or at least equal to the accumulated axial manufacturing tolerances of the components of the cartridge unit 2, e.g. the cartridge holder 4 and the cartridge 5, and the drive unit 3, e.g. the housing 7 and the piston rod 13. In this way, the accumulated axial manufacturing tolerances may be compensatable by means of the deformable member 33, in particular by deformation of the deformable member 33, when the cartridge unit 2 is secured to the drive unit 3. Despite manufacturing tolerances the drive unit 3 and the cartridge unit 2 may be secured to each other with a predetermined relative end position with respect to each other on account of the deformable member 33 which is deformed to compensate for the manufacturing tolerances. The amount of deformation may depend on the total accumulated manufacturing tolerances in the drive unit 3 and the cartridge unit 2. Thus, the axial extension of the deformable member 33 preferably depends on the previously determined measure for the manufacturing tolerances to allow for compensation of the manufacturing tolerances by deformation of the deformable member 33.

Alternatively or additionally, the accumulated axial manufacturing tolerances or a part thereof may be compensatable by means of the connection section 18C, in particular due to elastic deformation of the connection section 18C, when the cartridge unit 2 is secured to the drive unit 3. In this case, the connection section 18C may comprise an axial extension greater than the length of the oblique surface 39A, in particular greater than the accumulated axial manufacturing tolerances of the components of the cartridge unit 2 and the drive unit 3, when the connection section 18C is in an undeformed state. The deformable member 33 may be redundant or provided additionally in that case.

When the cartridge unit 2 is secured, e.g. screwed (see arrow 30 in FIG. 7B), to the drive unit 3, e.g. when the device 1 is assembled, the deformable member 33 may abut the drive part 18, in particular a proximal surface of the drive part 18. The deformable member 33 is deformed when the drive part 18, in particular connection means 24, is moved to be brought into mechanically cooperation with a connection means 25 of the piston rod 13 to operatively connect, preferably releasably operatively connect, in particular snap-fit, the drive part 18 to the piston rod 13. The connection means 25 may comprise a snap-fit member, for example an at least partly spherical bulge. The connection means 24 may comprise a curved cavity. The curved cavity may be surrounded by resilient fingers which are bowed radially outwardly with respect to the cavity when the connection means 25 engages with, in particular snap-fits to, connection means 24. An audible and/or tactile feedback may be given to the user when the drive part 18 is connected to the piston rod 13.

Due to the previously described manufacturing tolerances, the cartridge unit 2 and the drive unit 3 may not be positioned at their desired relative end position when mechanically cooperating. Accordingly, there may be a gap between the cartridge unit 2, in particular the proximal end of the cartridge unit 2, and the drive unit 3, in particular the distal end of the drive unit 3, arising from the manufacturing tolerances. The gap is indicated by arrow 44 in FIG. 7B. For closing the gap the cartridge unit 2 is displaced further in the proximal direction with respect to the drive unit 3 towards the desired end position with respect to the drive unit 3. Thereby, the deformable member 33 is further deformed. The deformable member 33 is deformed until the cartridge unit 2 has reached the desired end position with respect to the drive unit 3. Accordingly, when the cartridge unit 2 was secured to the drive unit 3, there is no gap between the drive unit 3 and the cartridge unit 2.

When the cartridge unit 2 was secured to the drive unit 3, the distal surface of the drive part 18 abuts the bung 17. If the deformable member 33 is elastically deformable, a restoring force of the deformable member 33 is expediently smaller than an adhesive force between the bung 17 and the cartridge 5 in order to prevent that the drive part 18 and, hence, the bung 17, are unintentionally displaced distally with respect to the cartridge 5 by the restoring force when the previously mentioned septum is pierced by the needle.

FIGS. 7A through 7C schematically show the drug delivery device of FIG. 1 while being assembled and after assembling was completed.

FIGS. 8A through 8C schematically show parts of the readily assembled drug delivery device.

FIG. 9 schematically shows a sectional view of the drug delivery device of FIG. 7C. In particular, FIG. 9 shows the drug delivery device 1 after assembling was completed.

For assembling the drug delivery device 1, e.g. for securing the cartridge unit 2 to the drive unit 3 the following steps are performed:

At first, the cartridge unit 2 is assembled, i.e. the cartridge 5 is secured in the cartridge holder 4 as described in connection with FIGS. 3, 4A and 4B. Accordingly, before the cartridge unit 2 is secured, preferably releasably secured, to the drive unit 3 all play may have been removed between moveable components of the cartridge unit 2, in particular between the cartridge 5 and the cartridge holder 4.

In a next step, the drive unit 3 is assembled as described in connection with FIGS. 5, 6A and 6B. Accordingly, before the cartridge unit 2 is secured, preferably releasably secured, to the drive unit 3 all play may have been removed between moveable components of the drive unit 3, in particular between the piston rod 13 and the drive member 14 (see arrow 35 in FIG. 9).

In a last step, the cartridge unit 2 is secured, for example screwed, to the drive unit 3 as described above. Thereby, a gap between the cartridge unit 2 and the drive unit 3 is removed by means of the deformable member 33. Dose accuracy may be increased in this way.

In the assembled drug delivery device 1 all play between components of the drug delivery device 1 which are moveable when dispensing the dose, in particular the cartridge 5, the cartridge holder 4, the drive part 18, the piston rod 13 and the bung 17, has been removed, in particular before a first dose delivery action may take place. Accordingly, after having assembled the drug delivery device 1, the device 1 is immediately ready for setting and delivering a dose of the drug 16. User-operated steps, e.g. priming steps, for removing play between the moveable components for setting and delivering a dose with high accuracy may be avoided. In this way, underdosing, which may have fatal or even lethal consequences for the user, may be prevented.

Preferably, as described in connection with FIG. 2, the cartridge unit 2 is releasably secured, in particular screwed, to the drive unit 3 (see FIG. 8B). In this case, the cartridge unit 2 may be unsecured from the drive unit 3 when the total amount of the drug 16 held in the cartridge 5 was dispensed (not explicitly shown). Afterwards, the respective moveable part 23 may be moved radially outwardly with respect to the main longitudinal axis 49 and the drive part 18 and the emptied cartridge 5 may be removed from the cartridge holder 4. Thereupon, a replacement cartridge may be introduced into the cartridge holder 4. The respective moveable part 23 may be moved back radially inwardly, thus securing the replacement cartridge in the cartridge holder 4 as described in connection with FIGS. 3 and 4. Finally, as described above, the drive unit 3 is assembled and the cartridge unit 2 is secured to the drive unit 3.

Alternatively, the cartridge unit 2 may be irreleasably secured to the drive unit 3, for example via a permanent snap-fit connection, as shown in FIG. 8C. For this purpose, the cartridge unit 2, in particular the cartridge holder 4, provides at least one engaging means 37. Engaging means 37 is arranged in the proximal end section of the cartridge holder 4. Engaging means 37 protrudes radially outwardly from the cartridge holder 4. Preferably, engaging means 37 is a radially outwardly protruding flange. The drive unit 3, in particular the housing 7, provides mating engaging means 38. Engaging means 38 is arranged in the distal end section of the housing 7. Preferably, engaging means 38 comprises a recess running around an inner surface of the housing 7. For irreversibly securing the cartridge unit 2 to the drive unit 3 engaging means 37 and engaging means 38 mechanically cooperate with each other when the cartridge unit 2 is secured to the drive unit 3 to form the permanent snap-fit connection. To unsecure the cartridge unit 2 from the drive unit 3 the connection would have to be solved by damage. This may facilitate provision of a non re-usable drug delivery device 1. Mechanical cooperation of engaging means 37 and engaging means 38 may give the user an audible and/or tactile feedback to indicate that the cartridge unit 2 and the drive unit 3 have been irreversibly connected to each other.

Other implementations are within the scope of the following claims. Elements of different implementations may be combined to form implementations not specifically described herein.

REFERENCE NUMERALS

1 Drug delivery device
2 Cartridge unit
3 Drive unit
4 Cartridge holder
5 Cartridge
6 Engaging means
7 Housing
8 Dose member
9 Dose button
10 Subsection
11 Distal end
12 Proximal end
13 Piston rod
13A Thread
14 Drive member
15 Engaging means
16 Drug
17 Bung
18 Drive part
18A Interaction section
18B Transition section
18C Connection section
19 Outlet
20 Stop member
21A Arrow
21B Arrow
23 Moveable part
24 Connection means
25 Connection means
26 Arrow
27 Stop member
28 Arrow
29 Arrow
30 Arrow
31 Arrow
32 Engaging means
33 Deformable member
34 Arrow
35 Arrow
37 Engaging means
38 Engaging means
39 Protrusion
39A Oblique side face
39B Free end
40 Thread
42 Opening
43 Protruding portion
44 Arrow
47 Main part
47A Shoulder portion
47B Cartridge retaining section
48 Cut-out
49 Main longitudinal axis
50 Interior

The invention claimed is:

1. A drug delivery device comprising:
a housing having a distal end and a proximal end;
a cartridge holder for retaining a section of a cartridge, the cartridge holder comprising a distal end and proximal end, and further comprising:
an opening arranged at the proximal end of the cartridge holder through which the section of the cartridge is insertable; and
a main part and a first moveable part that is moveably connected to the main part, wherein the first moveable part comprises a protrusion and wherein the first moveable part is arranged at or near the proximal end of the cartridge holder,
wherein the protrusion is arranged at an axial position for engaging proximally behind an edge of the section of the cartridge, and
wherein the cartridge holder comprises an engaging means at the proximal end,
wherein the housing comprises a counter engaging means at the distal end configured for the mechanical cooperation with the engaging means for securing the cartridge holder to the housing,
a drive unit, the drive unit comprising a drive member positioned within the housing and movable with respect to the housing; and
a piston rod at least partially within the drive member, the piston rod designed to transfer a force to a bung contained within the cartridge.

2. The drug delivery device of claim 1, wherein the first moveable part is arranged to define a radial extension of a subsection of an interior of the cartridge holder.

3. The drug delivery device of claim 2, wherein the subsection of the interior of the cartridge holder is arranged at an axial position that is further away from the distal end of the cartridge holder than the cartridge retaining section is.

4. The drug delivery device of claim 2, wherein
the first moveable part is arranged to vary the radial extension of the subsection of the interior of the cartridge holder when the first moveable part is moved with respect to the main part of the cartridge holder.

5. The drug delivery device of claim 1, further comprising a dose member positioned near the proximal end of the housing,
the dose member moveable to allow a dose of drug to be delivered by the drug delivery device.

6. The drug delivery device of claim 5, wherein
the dose member comprises a rotatable dose member.

7. The drug delivery device of claim 5, further comprising a dose button positioned near the proximal end of the housing.

8. The drug delivery device of claim 7 wherein
the dose button is separate from the dose member.

9. The drug delivery device of claim 7 wherein
the dose button is configured to be moved in a distal direction in order to dispense a dose of a drug.

10. The drug delivery device of claim 7 wherein
the dose button can move in the proximal direction.

11. The drug delivery device of claim 1, wherein
the drive member comprises a movable drive member.

12. The drug delivery device of claim 11, wherein
the movable drive member comprises a rotatable drive member.

13. The drug delivery device of claim 1, wherein the cartridge comprises:
a septum for sealing a distal end of the cartridge,
the septum being pierceable by a needle that is connected to the cartridge holder.

14. The drug delivery device of claim 1 wherein
the cartridge holder further comprises a second moveable part.

15. The drug delivery device of claim 14 wherein
the first moveable part is arranged opposite the second moveable part.

16. The drug delivery device of claim 1 wherein
the first moveable part and the main part of the cartridge holder are formed unitarily.

17. The drug delivery device of claim 1 wherein
the first moveable part is arranged near the proximal end of the cartridge holder.

18. The drug delivery device of claim 1 wherein
the first movable part comprises the engaging means.

19. The drug delivery device of claim 1 further comprising:
a drive part, the drive part comprising an interaction section arranged at a distal end of the drive part,
the interaction section configured to mechanically interact with a bung of a cartridge.

20. The drug delivery device of claim 19 wherein
the drive part comprises a protruding portion.

21. The drug delivery device of claim 20 wherein
the protruding portion of the drive part comprises a radially outwardly directed flange.

22. The drug delivery device of claim 19, wherein
the drive part comprises a distal end having a first outer diameter and a proximal end having a second outer diameter,
wherein the first out diameter of the drive part is different than the second outer diameter of the drive part.

23. The drug delivery device of claim 19, wherein
the drive part is connected to a distal end of the piston rod.

24. The drug delivery device of claim 1 wherein
the movable drive member comprises a rotatable cylindrical drive member,
the moveable drive member positioned within the housing and rotatable with respect to the housing to allow delivery of a dose.

25. The drug delivery device of claim 1 wherein
the drug delivery device is configured to dispense a fixed dose of a drug contained within a cartridge.

26. The drug delivery device of claim 1 wherein
the main part of the cartridge holder comprises a tubular main part;
the main part comprises a radially inwardly directed shoulder portion,
the radially inwardly directed shoulder portion forming a distal end stop face for the cartridge when the cartridge is inserted into the cartridge holder.

27. The drug delivery device of claim 19 wherein
the drive unit comprises a deformable member, the deformable member configured to mechanically interact with the drive part.

28. The drug delivery device of claim 27 wherein
the deformable member comprises two oppositely disposed deformable members.

29. The drug delivery device of claim 28 wherein
the two oppositely disposed deformable members comprise elastically deformable deflectable members.

30. The drug delivery device of claim 1, wherein the engaging means is provided in at least a portion of an outer surface of the first movable part.

31. The drug delivery device of claim 1, wherein the engaging means is an outer thread and wherein the counter engaging means is an inner thread.

32. The drug delivery device of claim 1, wherein the engaging means is a radially outwardly protruding flange and wherein the counter engaging means is a recess running along an inner surface of the housing.

* * * * *

UNITED STATES PATENT AND TRADEMARK OFFICE
CERTIFICATE OF CORRECTION

PATENT NO. : 10,376,646 B2
APPLICATION NO. : 14/815977
DATED : August 13, 2019
INVENTOR(S) : Philippe Nzike, Steffen Raab and Uwe Dasbach Page 1 of 1

It is certified that error appears in the above-identified patent and that said Letters Patent is hereby corrected as shown below:

On the Title Page

Item (71), Column 1, Line 1 of "Applicant:", delete "GmbH" and insert -- GmbH, Frankfurt am Main (DE) --

In the Claims

Column 20, Line 10, Claim 22, delete "out" and insert -- outer --

Signed and Sealed this
Fourth Day of February, 2020

Andrei Iancu
*Director of the United States Patent and Trademark Office*